US010765533B2

(12) United States Patent
Bonny et al.

(10) Patent No.: US 10,765,533 B2
(45) Date of Patent: Sep. 8, 2020

(54) SURVEYING TIBIAL TRIALS FOR KNEE ARTHROPLASTY

(71) Applicant: THINK SURGICAL, INC., Fremont, CA (US)

(72) Inventors: Daniel Patrick Bonny, Fremont, CA (US); Joel Zuhars, Fremont, CA (US)

(73) Assignee: THINK SURGICAL, INC., Fremont, CA (US)

( * ) Notice: Subject to any disclaimer, the term of this patent is extended or adjusted under 35 U.S.C. 154(b) by 0 days.

(21) Appl. No.: 15/526,230

(22) PCT Filed: Dec. 11, 2015

(86) PCT No.: PCT/US2015/065295
§ 371 (c)(1),
(2) Date: May 11, 2017

(87) PCT Pub. No.: WO2016/094826
PCT Pub. Date: Jun. 16, 2016

(65) Prior Publication Data
US 2017/0325973 A1 Nov. 16, 2017

Related U.S. Application Data

(60) Provisional application No. 62/090,660, filed on Dec. 11, 2014.

(51) Int. Cl.
A61F 2/46 (2006.01)
A61F 2/38 (2006.01)
A61F 2/30 (2006.01)

(52) U.S. Cl.
CPC ............ *A61F 2/4684* (2013.01); *A61F 2/389* (2013.01); *A61F 2002/30364* (2013.01);
(Continued)

(58) Field of Classification Search
CPC .............. A61F 2/389; A61F 2002/3895; A61F 2/3886; A61F 2002/3881; A61F 2/3868;
(Continued)

(56) References Cited

U.S. PATENT DOCUMENTS 5,733,292 A 3/1998 Gustilo et al.
5,782,925 A 7/1998 Collazo et al.
(Continued)

OTHER PUBLICATIONS

The International Search Report dated Apr. 1, 2016 for International Application PCT/US2015/065295 filed Dec. 11, 2015.
(Continued)

*Primary Examiner* — Alvin J Stewart
(74) *Attorney, Agent, or Firm* — Blue Filament Law PLLC

(57) ABSTRACT

A system and process for performing orthopedic surgery is provided that uses a tibial trial system in total knee arthroplasty for assessing optimal internal-external rotation and posterior tibial slope, and for measuring the rotation of a tibial trial throughout flexion-extension to determine and mark the best position for the final tibial component. The tibial trial system determines the internal-external location on a patient specific basis with improved component placement well within the present manual methods. One particular advantage to the tibial trial system is to assess the natural internal-external rotation that the tibial component will experience relative to the femoral component during flexion-extension as opposed to simply recording and balancing forces on a static tibial trial. The invention disclosed herein may also be adapted to be used with a computer assisted surgical device. Such surgical devices include active, semi-active, and haptic devices as well as articulating drill and saw systems.

18 Claims, 5 Drawing Sheets

(52) U.S. Cl.
CPC .............. *A61F 2002/30471* (2013.01); *A61F 2002/30476* (2013.01); *A61F 2002/30507* (2013.01); *A61F 2002/30538* (2013.01); *A61F 2002/30565* (2013.01); *A61F 2002/469* (2013.01); *A61F 2002/4668* (2013.01)

(58) Field of Classification Search
CPC ................... A61F 2/3859; A61F 2/38; A61F 2002/30087; A61F 2002/30558; A61F 2240/007; A61F 2240/008; A61F 2002/488; A61F 2002/4666; A61F 2002/4667; A61F 2/468; A61B 5/065; A61B 5/068; A61B 5/067; A61B 5/68
See application file for complete search history.

(56) References Cited

U.S. PATENT DOCUMENTS

| | | |
|---|---|---|
| 2003/0069644 A1 | 4/2003 | Kovacevic et al. |
| 2004/0019382 A1 | 1/2004 | Amirouche et al. |
| 2004/0054416 A1* | 3/2004 | Wyss .................... A61F 2/3868 623/20.27 |
| 2007/0233267 A1 | 10/2007 | Amirouche et al. |
| 2007/0234819 A1* | 10/2007 | Amirouche ............. A61F 2/389 73/781 |
| 2010/0125339 A1 | 5/2010 | Earl et al. |
| 2013/0261505 A1 | 10/2013 | Sherman et al. |
| 2014/0288464 A1 | 9/2014 | Stein |

OTHER PUBLICATIONS

Supplementary European Search Report dated Jun. 27, 2018 for European Application No. EP 15867152 filed Dec. 11, 2015.

* cited by examiner

SURVEYING TIBIAL TRIALS FOR KNEE ARTHROPLASTY

CROSS REFERENCE TO RELATED APPLICATIONS

This application claims priority benefit of U.S. Provisional Application Ser. No. 62/090,660 filed 11 Dec. 2014; the contents of which are hereby incorporated by reference.

FIELD OF THE INVENTION

The present invention relates generally to the field of joint replacement, and more specifically to a new and useful method for performing tibial trials used to survey internal-external rotation and posterior slope to optimize final tibial component positioning in knee arthroplasty.

BACKGROUND OF THE INVENTION

Total joint replacement (TJR) (also called primary total joint arthroplasty) is a surgical procedure in which the articulating surfaces of a joint are replaced with prosthetic components, or implants. It is a successful procedure, especially for hips, knees, shoulders, and ankles and allows people to restore functionality while greatly reducing pain associated with osteoarthritis.

Bone is a living tissue that is constantly changing through the resorption of matrix by osteoclasts and the deposition of new matrix by osteoblasts. Articular cartilage is an avascular tissue that is found on the surfaces of joints and serves to provide a smooth interface upon which bones can articulate with each other. Joint replacement arthroplasty is an orthopedic procedure in which the typically worn surface of the joint is replaced with a prosthetic component, or implant. Joint replacement arthroplasty typically requires the removal of the articulating cartilage surface of the joint including a varying amount of bone depending on the joint and the replacement implant being used. The articulating cartilage surface and bone is then replaced with a synthetic, typically metal implant that is used to create a new joint surface.

The correct placement of the femoral and tibial components in total knee arthroplasty has a direct impact on clinical outcomes and implant longevity. One particularly difficult placement parameter is the internal-external rotation of the tibial component on the tibia. Rotational malpositioning of the femoral or tibial component may result in flexion instability, component wear, deviated patellar tracking, and inadequate unsatisfactory joint kinematics, and pain.

During a conventional total knee arthroplasty, either with manual instruments or via computer navigation, a tibial trial component is used prior to implantation of the final tibial component. The tibial trial component is used to verify the size of the final component and to ensure the desired flexion-extension gap and ligament balancing has been achieved. To determine the correct internal-external rotation of the final component, two methods are commonly used. One method references an anatomical landmark whereby the component is aligned with the midsulcus of the tibial spine, the posterior condylar line of the tibia, the medial border of the tibial tubercle, or the medial ⅓ of the tibia tubercle. Another method allows the tibial trail to freely rotate throughout flexion and extension. The component is then aligned with the anterior position of the trial in extension and another reference point (e.g., center of tibia, posterior cruciate ligament (PCL)) on the tibia. However, clinical studies have shown that the final internal-external rotation of the component has a large patient intervariability using either method. In the first method, the tibial trial is fixed to the tibial plateau, making it difficult to determine the best axial rotation of the component. The anatomic landmarks used to identify the correct internal-external rotational alignment are also difficult to locate intraoperatively. The second method lacks in assessing the full range of internal-external rotation throughout flexion-extension.

Additionally, during knee arthroplasty, the posterior slope of the tibial cut is determined prior to using the provisional component, which makes it difficult to determine how much adjustment, if any, is needed in this degree of freedom. The final posterior tibial slope can have a significant impact on clinical outcomes, joint stability, joint kinematics, and implant longevity. Traditionally, the surgeon will try to restore the patient's natural slope and use a provisional component to ensure the ligaments are balanced. In some circumstances, the slope needs to be re-cut after the trial has been used, and the degree of angulation is determined based on the surgeon's judgment. However, because the tibia has already been cut, it can be difficult to determine how much angulation, if any, is needed when performing a recut of the tibia.

Therefore, there is a need for a tibial trial component that can assist a surgeon in consistently placing the final tibial implant component in the proper internal-external rotation. There is an additional need for a tibial trial component that can provide a surgeon with a quantitative measurement of a posterior tibial slope re-cut. There is a further need for a method to mark or assist with the proper positioning of the final component as determined by the tibial trial.

SUMMARY OF THE INVENTION

A tibial trial system is provided that includes a base component having an upper surface and a lower surface, and an articulating component having a superior surface and an inferior surface. The base component is connected to the articulating component by a rotary joint extending from the upper surface of the base. The upper surface of the base has at least one rotation sensor positioned thereon, where the rotary joint is engaged with the inferior surface of the articulating component so that the articulating component can rotate relative to the base component.

A method of using the tibial system is also provided that includes using a set of position marks generated by a computer assisted device to determine a placement position for the tibial trial component in a patient's knee joint. The tibial trial component is inserted in the determined placement position. A rotational position of the articulating component is registered to the base component, and the knee joint is articulated through flexion-extension, where the articulating component rotates with a femoral component and a series of measurements are made by the computer assisted device, where the computer assisted device records and determines an optimum internal-external rotation relative to the base component. Subsequently, the tibial trial component is removed to allow the computer assisted device to mill a keel hole for a final tibial component placement in the determined optimum internal-external orientation.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

DESCRIPTION OF THE INVENTION

The invention disclosed herein describes a tibial trial system in total knee arthroplasty for assessing optimal internal-external rotation and posterior tibial slope, but more particularly for measuring the rotation of a tibial trial throughout flexion-extension to determine and mark the best position for the final tibial component.

It is to be understood that in instances where a range of values are provided that the range is intended to encompass not only the end point values of the range but also intermediate values of the range as explicitly being included within the range and varying by the last significant figure of the range. By way of example, a recited range from 1 to 4 is intended to include 1-2, 1-3, 2-4, 3-4, and 1-4.

The invention disclosed herein has utility in assisting a surgeon to locate and mark on the tibia the optimum internal-external rotation for a final tibial implant with respect to the femoral implant in total knee arthroplasty. It should be appreciated that the tibial trial system may determine the internal-external location on a patient specific basis with improved component placement well within the present manual methods. One particular advantage to the tibial trial system is to assess the natural internal-external rotation that the tibial component will experience relative to the femoral component during flexion-extension as opposed to simply recording and balancing forces on a static tibial trial.

The invention disclosed herein may also be adapted to be used with a computer assisted surgical device. Such surgical devices include active, semi-active, and haptic devices as well as articulating drill and saw systems. Generally, pre-operative planning allows a user to plan a total knee arthroplasty case and transfer the plan to the computer assisted surgical device. The device may then aid the surgeon in making the appropriate cuts on the femur and tibia to match the pre-operative plan. However, the internal-external rotation of the component is still planned based on anatomic landmarks as seen on either two-dimensional radiographs or three-dimensional bone models. It will be appreciated that the disclosed invention in conjunction with a computer assisted device may greatly improve the final tibial implant position in terms of external-internal rotation and tibial slope.

Figure 1A:
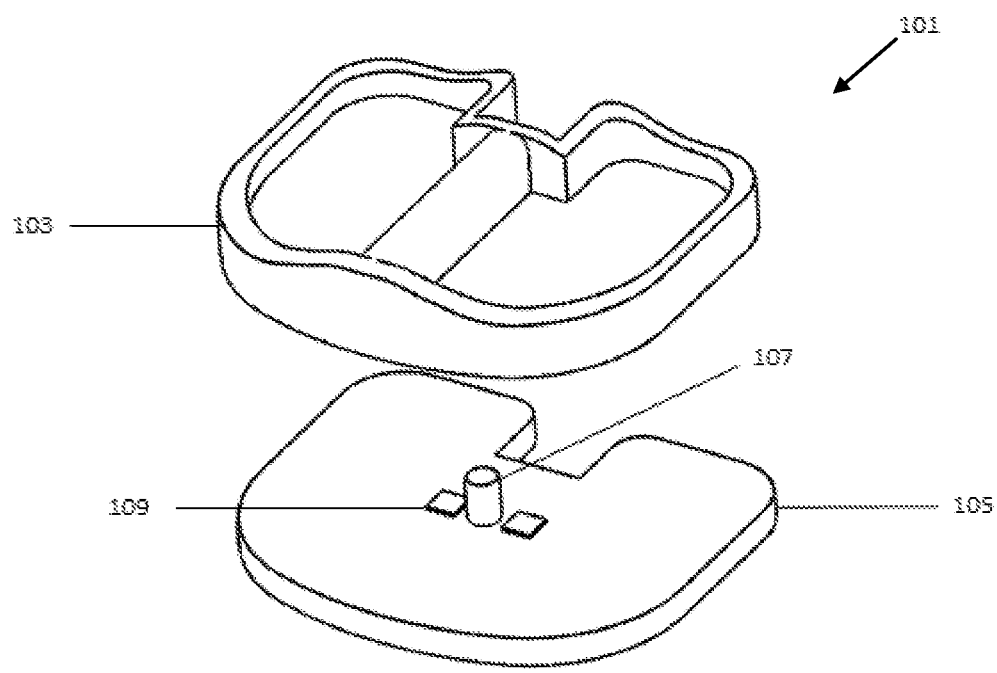
FIGS. 1A and 1B generally illustrate two perspective views of a tibial trial system in accordance with an embodiment of the present invention.
Figure 1B:
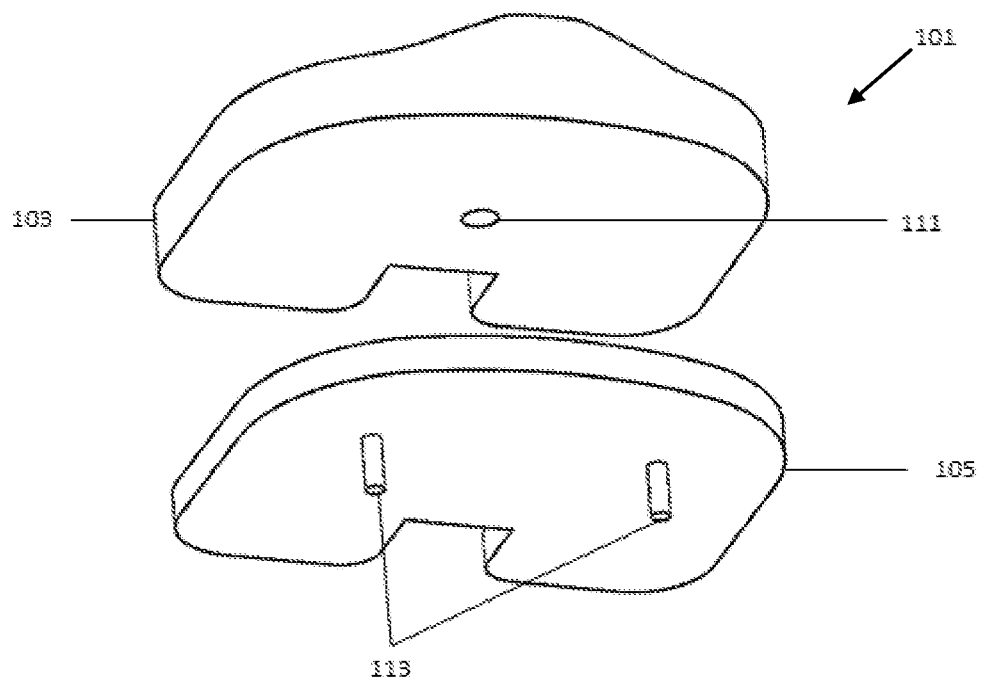

Referring now to the figures, FIGS. 1A and 1B generally show a tibial trial system 101 in accordance with embodiments of the invention. The main components in the specific embodiment of the tibial trial system 101 include an articulating component 103, a base component 105, a rotary joint 107, and at least one rotational sensor 109 between the articulating component 103 and the base component 105. The rotary joint 107 is connected to the base component 105 and to the tibial tray component at engagement hole 111 so the articulating component 103 can rotate relative to the base component 105. The base component 105 also has at least one anchoring mechanism 113 to attach to the tibial plateau of a patient.

The rotary joint 107 connects the articulating component 103 to the base component 105. In one embodiment the rotary joint 107 connects the articulating component 103 and base component 105 at their geometric centers. The rotary joint 107 can be any mechanism that allows the articulating component 103 to rotate relative to the base component 105. In one embodiment, the rotary joint 107 is rigidly fixed to the base component 105 and to the articulating component 103, whereby the rotation occurs on the rotary joint 107 between the articulating component 103 and the base component 105. In another embodiment the rotary joint 107 is fixed to the base component 105, and the rotary joint 107 attaches to the articulating component 103 whereby the rotation occurs between the connection between the rotary joint 107 and the articulating component 103. In an alternative embodiment the rotary joint 107 is fixed to the articulating component 103 and attaches to the base component 105 whereby the rotation occurs between the connection between the rotary joint 107 and the base component 105.

The base component 105 attaches to the tibial plateau of the patient after the surgeon has made the tibial cut. In one embodiment, the base component 105 has two small protrusions 113 that can fit into two complimentary holes made on the tibial plateau of the patient. Therefore the base component 105 is fixed to the tibial plateau in a designated spot. The articulating component 103 may then rotate with the femoral trial component on the femur during flexion-extension of the knee to assess component sizing, flexion-extension gap, ligament balancing and internal-external rotation. In one embodiment, the tibial trial system 101 is assembled as one unit. In another embodiment, there are multiple articulating components that the surgeon can choose from. For example, different sizes, shapes, slopes, etc. of the articulating component may be assembled onto the base component intra-operatively to assess the final tibial component size, flexion-extension gap, ligament balancing, etc. The components 103 and 105 are readily formed of materials conventional to orthopedic surgical aids, these materials illustratively include plastics, steel, aluminum, or brass. It is appreciated that a plastic component is readily formed so as to be transparent to provide for visual inspection of underlying surfaces.

At least one rotation sensor 109 is integrated between the articulating component 103 and the base component 105. The rotation sensor/s 109 may be attached to or within the articulating component 103, the base component 105, rotary joint 107, or any combination thereof. The rotation sensor/s 109 may be any sensor capable of measuring rotation such as but not limited to a potentiometer, Hall Effect sensor, encoder, rotary variable differential transformer, resolver, etc. The rotation sensor/s 109 measures the amount of rotation that occurs between the base component 105 and the articulating component 103. In one embodiment, once the tibial trial 101 is positioned on the patient's tibial plateau and the knee is placed in full extension, the sensor 109 is zeroed. The surgeon then articulates the knee through flexion-extension and the sensor 109 measures and records the angle between the articulating component 103 and the base component 105. At least one processor (not shown) may be incorporated with the tibial trial system 101 to process the rotational data. In another embodiment, the tibial trial system 101 incorporates at least one memory storage unit (not shown) to store the rotational data. The tibial trial system 101 may also include a mechanism to lock the articulating component 103 in a desired internal-external rotation. The user may then assess the knee in flexion and extension with the articulating component 103 locked in the desired internal-external rotation.

In one specific embodiment, the data is sent to an external device by a physical wired or wireless connection. The external device could be for example a computer, a monitor, a computer assisted surgical device, an optical tracking system, a smart phone, heads up display (HUD) unit, glasses (such as Google glasses), etc., and any combination thereof. The physical connection could be by any electrical means connected to the tibial trial system 101 and to the external device. The data could be sent wirelessly from a transmitting device (not shown) on the tibial trial system 101 in communication with the rotation sensor/s 109 and/or processor/s incorporated with the tibial trial system 101. The data could be sent wirelessly for example via Bluetooth, Internet connection, radiofrequency, electromagnetic, visible light, targeted visible light, infrared, etc. In the case of transmitting data using visible light, in one embodiment, the tibial trial system 101 may incorporate active light emitting diodes (LEDs) in communication with the processor/s and/or rotation sensor/s 109.

Figure 4:
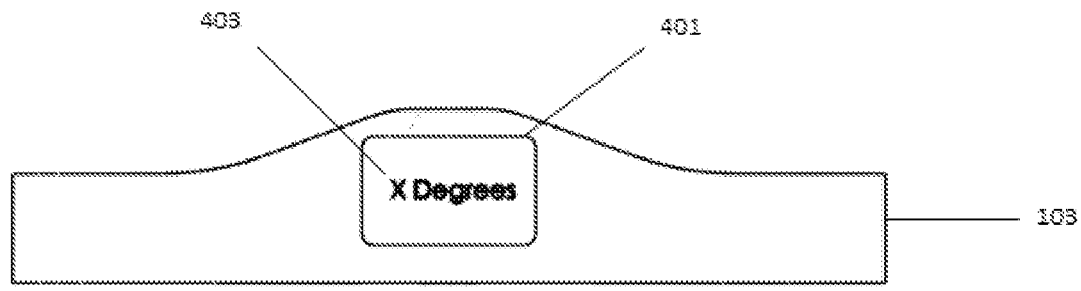
FIG. 4 illustrates an on-board display of the tibial trial system in accordance with an embodiment of the invention.

In another embodiment, with respect to FIG. 4, the rotational data 403 may be read from a display 401 incorporated with the tibial trial system 101. The display 401 may be incorporated on the articulating component 103 and/or the base component 105. The types of rotational data displayed and/or sent to an external device may include for example the rotational range, a mean value, a median value, etc. that indicates an optimum internal-external rotation for the final tibial component. In one embodiment, the user may select what information is displayed on the display unit 401.

Once a value has been indicated to the surgeon as to the optimum internal-external rotation placement, the tibial trial system 101 may have features to allow the surgeon to mark the position for the final component. In one embodiment, with respect to FIG. 2, the articulating component 103 has at least one hole 201, and the base component 105 has at least one corresponding groove 203. The groove 203 having a semi-circular or circular design to correspond with the rotation of the hole 201 as the articulating component 103 rotates relative to the base component 105. Therefore, the surgeon may mark on the tibial plateau at any rotation of the articulating component 103. In one embodiment, the spacing or geometry of the hole/s 201 and groove/s 203 is unique to a specific line of manufactured final tibial components so the markings will easily align to correctly place and/or prepare the keel for the final tibial component.

Figure 2:
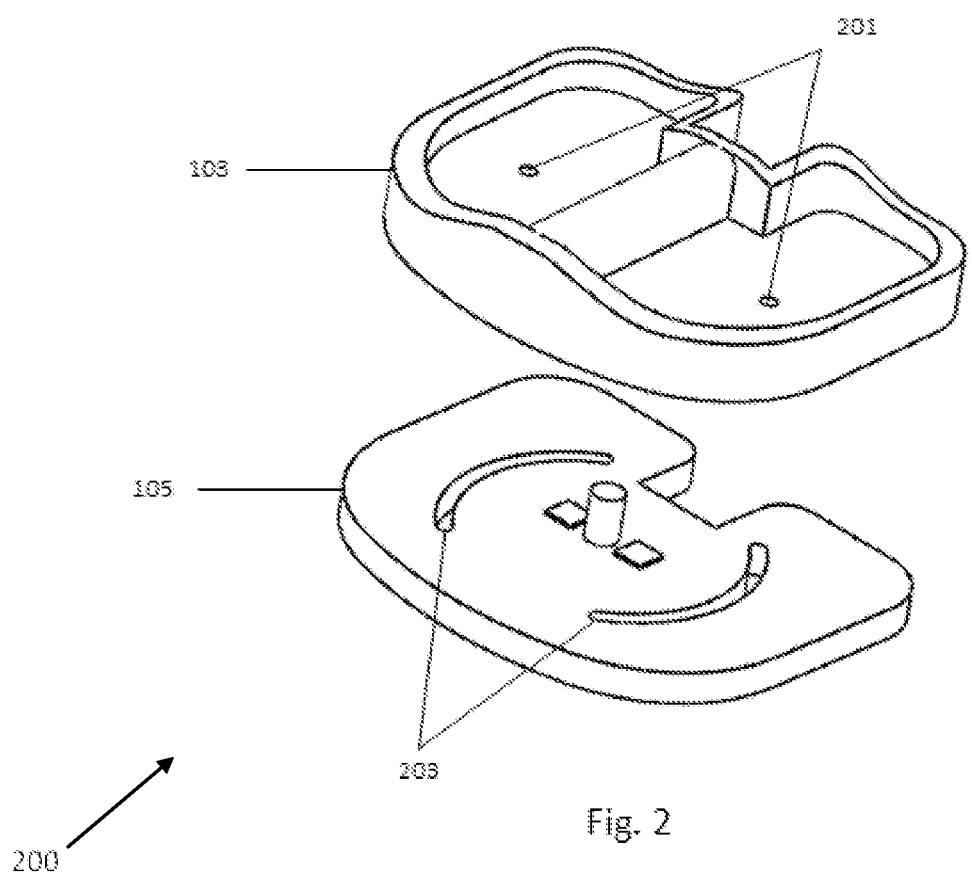
FIG. 2 depicts the tibial trial system depicted in FIGS. 1A and 1B with additional axial holes for marking the final tibial component in accordance with an embodiment of the invention.

If the holes 201 are positioned as shown in the example of FIG. 2 for an embodiment of the tibial trial system 200, the surgeon may have to gain access to the holes 201 by flexing and/or distracting the knee or even remove the femoral trial component. In this embodiment, once the surgeon has access to the holes 201, the surgeon may rotate the articulating component to the optimum internal-external external rotation that was determined during the trialing. The angle or rotation of the articulating component can be displayed an external device or the tibial trial system display 401, and once the angles or rotation have matched the optimum internal-external rotation, the surgeon can mark the tibial plateau through the hole/s 201 and groove/s 203.

Figure 3A:
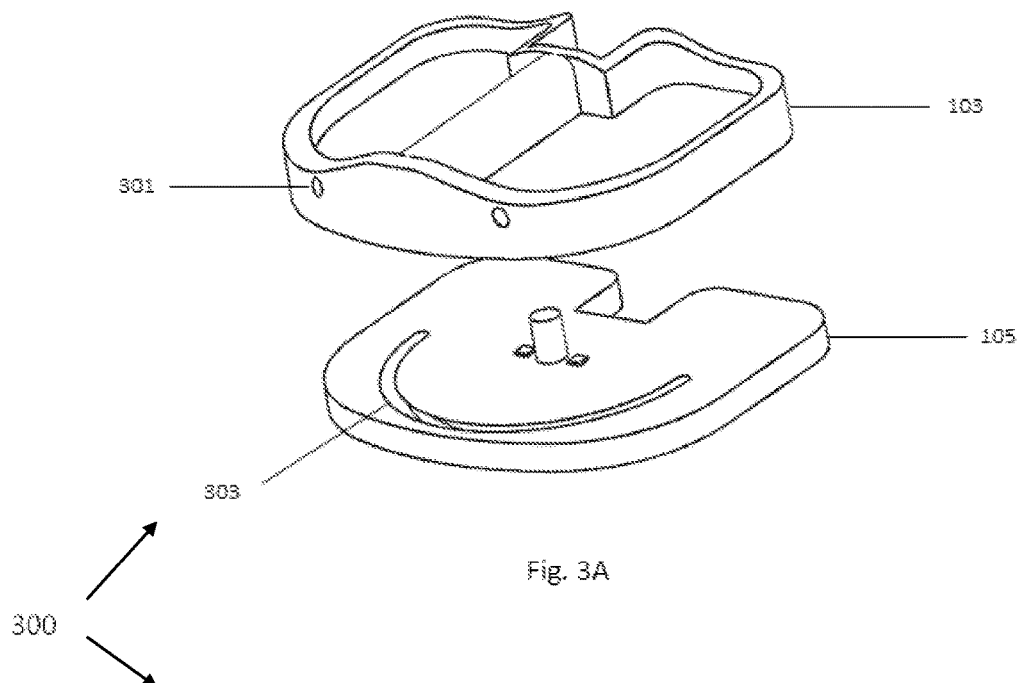
FIGS. 3A and 3B depict a perspective (FIG. 3A) and cross-sectional (FIG. 3B) view of the tibial trial system with coronal holes for marking the final tibial component in accordance with an embodiment of the invention.
Figure 3B:
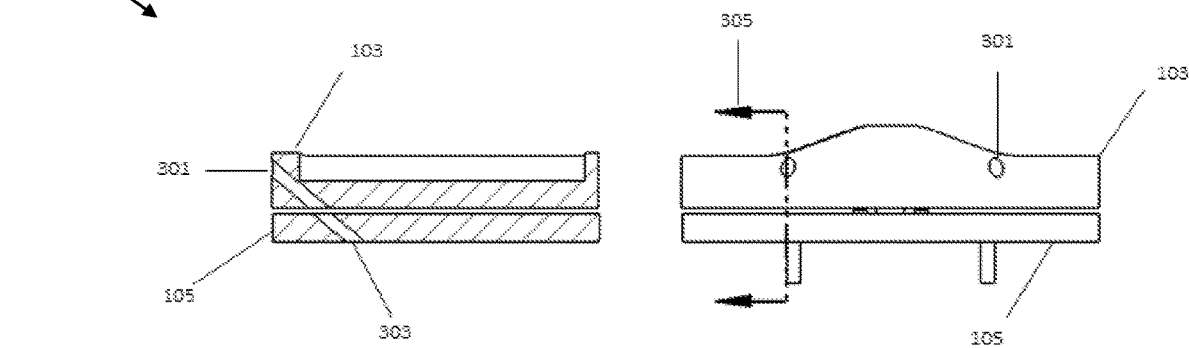

In an embodiment of the tibial trial system 300, with respect to FIGS. 3A and 3B, the hole/s 301 and groove/s 303 are positioned to allow the surgeon to mark the tibial plateau without having to flex, distract and/or remove the femoral trial component. The holes 301 are positioned on the front of the articulating component 103 and the grooves 303 of the base component 105 are angled to provide access to mark the tibial plateau. The grooves 303 likewise are semi-circular and/or circular to correspond with the holes 301 as the articulating component 103 rotates relative to the base component 105. FIG. 3B depicts a cross sectional view at 305 of the tibial trial system illustrating the access the surgeon has to mark the tibial plateau. In one embodiment, the spacing or geometry of the holes 301 is unique to a specific line of manufactured final tibial components so the markings will easily align to correctly place and/or prepare the keel for the final tibial component.

Tibial Posterior Slope

During the preparation of the tibial plateau, the posterior tibial slope cut is performed before trial reduction. A tibial trial system 101 may also include a rotary joint that allows for incremental changes in the amount of tibial posterior slope. The tibial trial system similarly has an articulating component, a base component and at least one rotary joint connecting the two components. The trial system additionally has a mechanism that allows the user to adjust the posterior slope during trial reduction. Before trialing, the slope may be set to a neutral position corresponding to the initial tibial slope cut. During flexion-extension of the knee, the user may assess the laxity and stability and adjust the slope accordingly. For example, if the knee is tight in extension then the surgeon can reduce the slope incrementally to reduce tightness. If the knee is tight in flexion then the surgeon can increase the tibial slope incrementally to reduce tightness. If the tibiofemoral joint dislocates, the tibial slope can be adjusted to improve conformity of the posterior articular surface. When the surgeon is satisfied with the patient's range of motion, laxity, and stability, the surgeon reads the required change from an indicator and uses that information to adjust the posterior slope.

Figure 6:
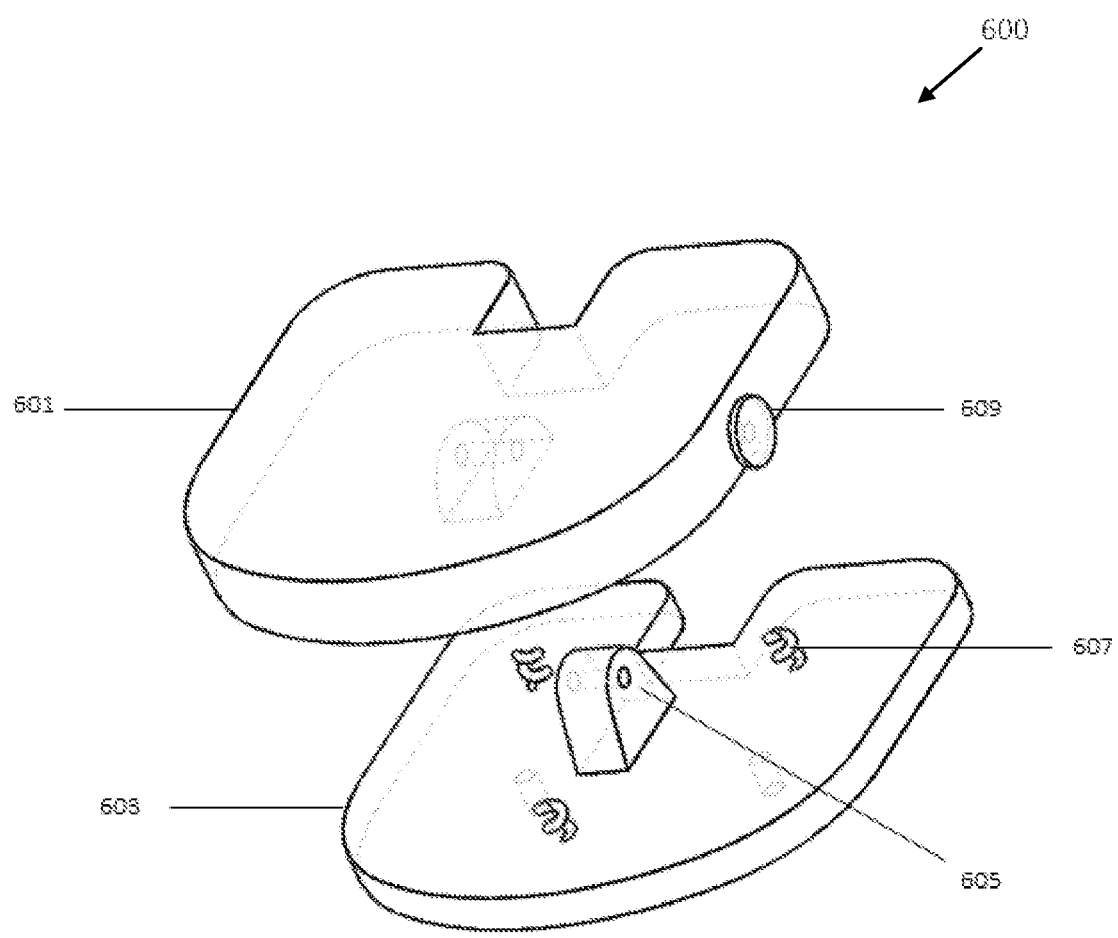
FIG. 6 is a perspective view of a tibial trial system configured with a rotary joint in accordance with an embodiment of the invention, where non-visible surfaces are shown in ghost.

The change in slope can be by any mechanical or electrical means that allows for a change in slope. For example, a rotary joint may be rigidly fixed to the base component 105 with a connection to the articulating component 103. Worm gears, hinges, screws, actuators, springs, bearings, ratchets, step motors, etc., may be assembled in a manner that allows the user to adjust the slope and maintain that slope throughout flexion and extension of the knee. An illustrative example is shown in FIG. 6. FIG. 6 is a perspective view of a tibial trial system 600 configured with a rotary joint in accordance with embodiments of the invention A hinge joint 605 connects the base component 603 and the articulating component 601. An adjustable knob 609 may be used to incrementally adjust and lock the slope of the articulating component 601 relative to the base 603. A ratcheting mechanism (not shown) could be used to lock the articulating component 601 in the desired slope. In one embodiment, springs 607 are attached between the articulating component 601 and the base component 603 for added support during flexion and extension. In another embodiment, a step motor (not shown) may be placed inside the articulating component 601 in connection with the hinge 605. The user may adjust the slope electrically with controls on the trial system or from an external device in communication with the step motor.

The base component 603 of the tibial trial slope system may be smaller in shape than the articulating component 601. The smaller shape may provide a greater degree of total slope change for the articulating component 601. For example, the base component can be 10% to 99% of the size of the articulating component 601 so the top of the base component 603 does not interfere with the anterior, posterior, medial or lateral edges of the articulating component 601 as the user adjusts the slope.

In one embodiment, the user may manually adjust the slope using a dial, knob, wing nut, screw, etc. One turn or set amount of manual adjustment could result in an x degree of slope change. For example, a wing nut that is rotated 180 degrees may result in a 1 degree change in slope. In another embodiment, the rotation may be done by pushing an up or down button whereby the slope change is controlled electronically. In one embodiment, anterior portion and the posterior portion of the trial system may be adjusted independently. In another embodiment, the medial portion and lateral portion of the trial system may be adjusted independently. Slope changes in the medial and lateral portion of the trial system may allow a user to assess the varus and valgus of the patient throughout flexion-extension and make any adjustments necessary in this degree of freedom. The tibial trial system can be capable of registering the initial slope when the user installs the trial system. As the user changes the slope, the change in degrees may be sent by wire or wirelessly to an external device as explained above.

In another embodiment, the tibial trial system may both rotate relative to the base as well as have the capability to change the slope. Therefore the tibial trial system would have two degrees of freedom in assessing the proper orientation of the final tibial component as well as assess any changes needed for the posterior tibial slope. In one embodiment, the tibial trial system is assembled as one unit. In another embodiment, multiple articulating components can be assembled onto the base component to assess the proper size of the final tibial tray.

Computer Assisted Procedures

Figure 5:
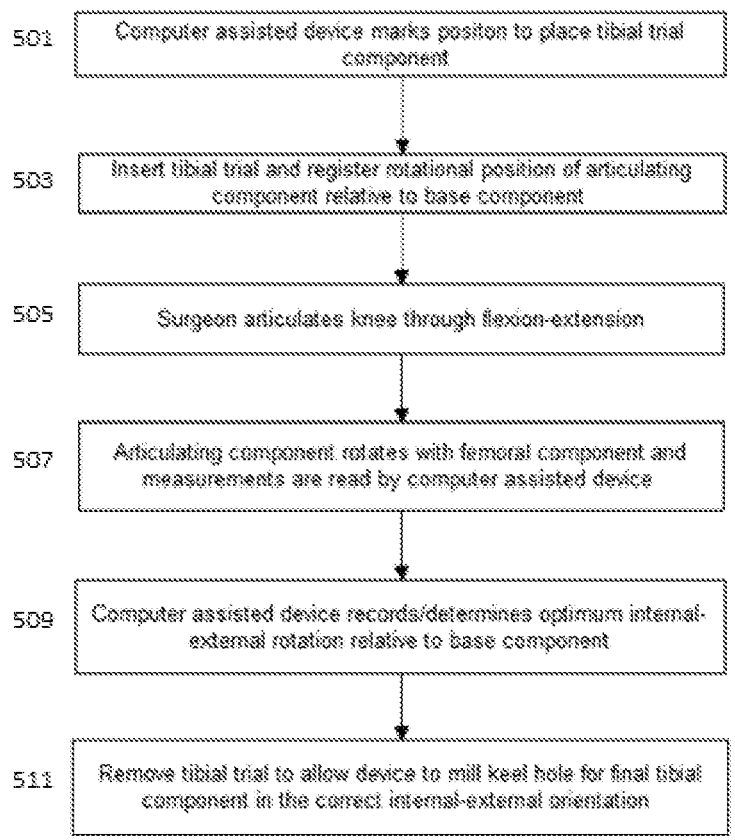
FIG. 5 is a flowchart outlining steps to use the tibial trial system with a computer assisted surgical device in accordance with an embodiment of the invention.

The tibial trial system 101 may similarly be used with a computer assisted surgical device to help aid in assessing the correct internal-external rotation and tibial slope of the final tibial component. With reference to FIG. 5, a computer assisted device may make the holes for the tibial trial system 501. For example, holes that match the protrusion 113 of the base component on the tibial plateau. The holes may be made based upon a pre-operative plan, registered intra-operatively with for example a digitizer, or marked by an optically tracked device. In one embodiment, the computer assisted device is an optically tracked articulating drill system that can mark the position of the holes on tibial plateau with the tip of the drill. The positions may then be registered with the tracking system relative to the bone whereby the tracking system will then maintain the articulating drill in the position to accurately mill the holes. In another embodiment, the computer assisted device is an active system. The active system may actively drill the holes for the tibial trial system 101 based upon a preoperative plan or communicated to the device using registration techniques such as a mechanical or optical digitizer.

Once the holes have been milled, the user may place the tibial trial system onto the tibial plateau 503. The user then articulates the knee throughout flexion-extension 505. The articulating component rotates with the femoral component relative to the base component and the angular and/or rotational measurements are sent by wire or wirelessly and read by external device 507. The external device processes the data as to the optimum internal-external rotation and/or adjustments to the tibial slope 509. In one embodiment of the inventive system, the optimum internal-external rotation and/or tibial slope adjustments is shown to the user for confirmation. After trialing, the computer assisted device may mill the keel hole in the correct orientation to place the final tibial component. In one embodiment, the computer assisted device is capable of cutting the keel actively 511. In another embodiment, a computer assisted device unable to make the cut may still mark the correct position on the tibial plateau whereby the user can then align manual instruments to make the correct keel hole in the proper orientation.

Other Embodiments

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient road map for implementing the exemplary embodiment or exemplary embodiments. It should be understood that various changes can be made in the function and arrangement of elements without departing from the scope as set forth in the appended claims and the legal equivalents thereof.

The invention claimed is:

1. A tibial trial system comprising:
a base component having an upper surface and a lower surface;
an articulating component having a superior surface and an inferior surface;
a rotary joint extending from the upper surface of the base;
at least one rotation sensor positioned on the upper surface, said rotary joint engaged with the inferior surface of said articulating component so that said articulating component can rotate relative to the base component; and
a lock to secure said articulating component in a desired internal-external rotation.

2. The tibial system of claim 1 wherein said rotary joint connects said articulating component and said base component at their geometric centers.

3. The tibial system of claim 1 wherein said rotary joint is rigidly fixed to the base component and to said articulating component to induce rotation on said rotary joint.

4. The tibial system of claim 1 further comprising a plurality of articulating components that vary from one another in at least one parameter of size, shape, slope so as to assess a final tibial component size, flexion-extension gap, or ligament balancing.

5. The tibial system of claim 1 wherein said at least one rotational sensor comprises at least one of: a potentiometer, Hall Effect sensor, encoder, rotary variable differential transformer, or a resolver.

6. The tibial system of claim 1 further comprising at least one processor to process a set of rotational data supplied from said at least one rotational sensor.

7. The tibial system of claim 1 further comprising at least one memory storage unit to store the rotational data supplied from said at least one rotational sensor.

8. The tibial system of claim 1 wherein said at least one rotation sensor provides rotational data to a display incorporated on said articulating component or on said base component.

9. A tibial trial system comprising:
   a base component having an upper surface and a lower surface;
   an articulating component having a superior surface and an inferior surface;
   a rotary joint extending from the upper surface of the base;
   at least one rotation sensor positioned on the upper surface, said rotary joint engaged with the inferior surface of said articulating component so that said articulating component can rotate relative to the base component; and
   an aperture on at least one of said superior surface or a front face of said articulating component and a corresponding groove on said base component, said groove having a semi-circular or circular design to correspond with a rotation of said aperture as said articulating component rotates relative to said base component.

10. The tibial trial system of claim 1 wherein said base component further comprises at least one anchoring mechanism to attach said base component to a tibial plateau of a patient's tibia bone.

11. The tibial trial system of claim 10 wherein said at least one anchoring mechanism has two protrusions from said lower surface that can fit into two complimentary holes made on the tibial plateau of the tibia bone of the patient.

12. The tibial system of claim 1 wherein said at least one rotational sensor provides a set of data via a wired or a wireless connection to an external device.

13. The tibial system of claim 12 wherein said external device comprises at least one of: a computer, a monitor, a computer assisted surgical device, an optical tracking system, a smart phone, a heads up display (HUD) unit, wearable display glasses and headgear, or any combination thereof.

14. The tibial system of claim 12 wherein said wireless connection comprises at least one of Bluetooth, Internet connection, radiofrequency, electromagnetic, visible light, targeted visible light, or infrared.

15. The tibial system of claim 14 wherein if said data is transmitted using visible light then said tibial system employs one or more active light emitting diodes (LEDs).

16. A tibial trial system comprising:
   a base component having an upper surface and a lower surface;
   an articulating component having a superior surface and an inferior surface;
   a rotary joint extending from the upper surface of the base;
   at least one rotation sensor positioned on the upper surface, said rotary joint engaged with the inferior surface of said articulating component so that said articulating component can rotate relative to the base component; and
   a rotary joint that allows for incremental changes in the amount of tibial posterior slope between said base component and said articulating component.

17. The tibial system of claim 16 wherein said rotary joint further comprises at least one of: worm gears, hinges, screws, actuators, springs, bearings, ratchets, or step motors; and wherein the slope of said rotary joint is controlled by manually or electrically via an adjustment knob.

18. A method of using a tibial trial system comprising a base component having an upper surface and a lower surface; an articulating component having a superior surface and an inferior surface; a rotary joint extending from the upper surface of the base; and at least one rotation sensor positioned on the upper surface, said rotary joint engaged with the inferior surface of said articulating component so that said articulating component can rotate relative to the base component, said method comprising:
   using a set of position marks generated by a computer assisted device to determine a placement position for said tibial trial system in a patient's knee joint;
   inserting said tibial trial system in the determined placement position;
   registering a rotational position of said articulating component to said base component;
   articulating the knee joint through flexion-extension, where said articulating component rotates with a femoral component and a series of measurements are made by the computer assisted device, where the computer assisted device records and determines an optimum internal-external rotation relative to said base component; and
   removing said tibial trial component to allow the computer assisted device to mill a keel hole or mark a position for the keel hole for a final tibial component placement in the determined optimum internal-external orientation.

* * * * *